United States Patent
Davenport et al.

(10) Patent No.: US 10,665,343 B1
(45) Date of Patent: May 26, 2020

(54) MEDICAL TREATMENT RECORD INTEGRATION

(71) Applicant: CERNER INNOVATION, INC., Kansas City, KS (US)

(72) Inventors: Mark A. Davenport, Overland Park, KS (US); Grant M. Damas, Olathe, KS (US); Tiffany L. Bateson, Kansas City, KS (US); Stephanie S. Greble, Raymore, MO (US); Molly Catherine Willman, Prairie Village, KS (US); Ramkumar Bommireddipalli, Overland Park, KS (US); John Q. DeVerter, Liberty, MO (US); Chao Shi, Silver Spring, MD (US)

(73) Assignee: CERNER INNOVATION, INC., Kansas City, KS (US)

( * ) Notice: Subject to any disclaimer, the term of this patent is extended or adjusted under 35 U.S.C. 154(b) by 1142 days.

(21) Appl. No.: 14/585,498

(22) Filed: Dec. 30, 2014

Related U.S. Application Data

(60) Provisional application No. 62/058,953, filed on Oct. 2, 2014.

(51) Int. Cl.
  *G16H 50/20* (2018.01)
  *G06N 5/04* (2006.01)
(52) U.S. Cl.
  CPC ............. *G16H 50/20* (2018.01); *G06N 5/045* (2013.01)
(58) Field of Classification Search
  CPC .............................. G16G 50/20; G06N 5/045
  See application file for complete search history.

(56) References Cited

U.S. PATENT DOCUMENTS

| | | | |
|---|---|---|---|
| 6,807,531 B1 | 10/2004 | Kanai | |
| 8,548,828 B1* | 10/2013 | Longmire | G06Q 10/10 705/3 |
| 2002/0091687 A1 | 7/2002 | Eglington | |
| 2005/0015278 A1 | 1/2005 | Ghouri | |
| 2005/0273363 A1 | 12/2005 | Lipscher et al. | |
| 2006/0265245 A1 | 11/2006 | McCallie et al. | |
| 2007/0027711 A1 | 2/2007 | Beraja et al. | |

(Continued)

OTHER PUBLICATIONS

First Action Interview Preinterview Communication dated Apr. 21, 2017 in U.S. Appl. No. 14/585,493, 5 pages.

(Continued)

*Primary Examiner* — Vincent Gonzales
*Assistant Examiner* — Kevin W Figueroa
(74) *Attorney, Agent, or Firm* — Shook, Hardy & Bacon L.L.P.

(57) ABSTRACT

Methods, systems, and computer-readable media are provided to suggest a medical course of action for a patient. Based on a diagnosis, a medical treatment decision tree is identified and integrated into an electronic medical record (EMR) of the patient. A series of branching nodes in the medical treatment decision tree are processed until a node with a suggested medical course of action for the patient is satisfied. The suggested course of action is exported. A medical procedure based on the suggested course of action is ordered and integrated into the medical treatment decision tree located in the EMR of the patient. It is then documented that the medical procedure was ordered in the treatment decision tree located in the EMR of the patient.

17 Claims, 15 Drawing Sheets

(56) References Cited

U.S. PATENT DOCUMENTS

| | | | |
|---|---|---|---|
| 2009/0125322 A9 | 5/2009 | Dahlin et al. | |
| 2011/0029322 A1* | 2/2011 | Hindo | G06F 19/325 |
| | | | 705/2 |
| 2012/0109689 A1 | 5/2012 | Lee | |
| 2012/0179482 A1 | 7/2012 | Garms | |
| 2012/0215558 A1 | 8/2012 | Flanagan et al. | |
| 2012/0269420 A1 | 10/2012 | Najarian et al. | |
| 2013/0006649 A1 | 1/2013 | Rangadass et al. | |
| 2013/0035956 A1 | 2/2013 | Carmeli et al. | |
| 2013/0079599 A1* | 3/2013 | Holmes | G06F 19/366 |
| | | | 600/300 |
| 2014/0100861 A1* | 4/2014 | Ledet | G06F 19/3443 |
| | | | 705/2 |
| 2015/0019241 A1 | 1/2015 | Bennett et al. | |
| 2015/0106111 A1* | 4/2015 | Gray | G06F 19/345 |
| | | | 705/2 |
| 2015/0248525 A1* | 9/2015 | Ury | G06Q 50/24 |
| | | | 705/3 |
| 2015/0310573 A1* | 10/2015 | Grant | G06Q 50/22 |
| 2016/0004827 A1* | 1/2016 | Silva | G06Q 10/101 |
| | | | 706/46 |
| 2016/0203281 A1 | 7/2016 | Zalis et al. | |

OTHER PUBLICATIONS

First Action Interview Office Action dated Jun. 14, 2017 in U.S. Appl. No. 14/585,493, 8 pages.
Final Office Action dated Dec. 20, 2017 in U.S. Appl. No. 14/585,493, 32 pages.
First Action Interview Preinterview Communication dated Aug. 11, 2017 in U.S. Appl. No. 14/585,488, 7 pages.
First Action Interview Office Action dated Nov. 2, 2017 in U.S. Appl. No. 14/585,488, 8 pages.
Non-Final Office Action received for U.S. Appl. No. 14/585,488, dated Sep. 19, 2018, 31 pages.
Final Office Action received for U.S. Appl. No. 14/585,488, dated Apr. 4, 2018, 29 pages.

* cited by examiner

FIG. 3A.

ADAMS, CHARLES – OPENED BY CARTER MD, JAN
TASK  EDIT  VIEW  PATIENT  CHART  LINKS

ADAMS, CHARLES⊠
ADAMS, CHARLES   DOB: 12/21/1989   AGE: 33 YEARS    SEX: MALE         ⇔LIST ⇦ |🗁 RECENT▾|
                 WEIGHT 167 LBS.   MRN: 200365448   FIN: 1005 63251   ALLERGIES: PENICILLIN, SHELLFISH

◊ ▸ ⌂ ONCOLOGY                                                        🖨 PRINT ⏱ 5 MINUTES AGO

PROSTATE ADENOCARCINOMA CLINICAL STAGE: IIA | PATHOLOGICAL STAGE: IA
LUNG LOREM IPSINOMA CLINICAL STAGE: IIA | PATHOLOGICAL STAGE: IA

| ONCOLOGY SUMMARY | FLOWSHEET | STAGING | FEBRILE NEUTROPENIA | WORKFLOW | PATHWAY |

PROSTATE ADENOCARCINOMA

● INITIAL WORKUP
  ○ 1ˢᵀ LINE METASTATIC
    TREATMENT

REVIEW

DOCUMENTS
 ╱408
TUMOR MARKERS

DIAGNOSTICS

PATHOLOGY

VITALS AND MEASUREMENTS

DOCUMENTS ✚                          LAST 24 HOURS | LAST MONTH | YEAR▾
                                     ☐ MY NOTES ONLY | ALL NOTE TYPES▾

┌─────────────────────────────────┬──────────────────────────────────────────────────────┐
│ CT ABDOMEN W/O CONTRAST          │ CT ABDOMEN W/O CONTRAST         SEP 26, 2013 1:28PM │
│ HAYDEN MD, SHILO   6 DAYS AGO    │                                                      │
│  ╲402                            │ * FINAL REPORT *                                     │
│ CT PELVIS WITH CONTRAST          │ REASON FOR EXAM ╱404                                 │
│ HAYDEN MD, SHILO   6 DAYS AGO    │ RULE OUT LIVER METASTESIS. LIVER FUNCTION TEST WNL   │
│                                  │ IMPRESSION: ╱404       ╱406                          │
│ NM BONE SCAN TOTAL BODY          │ CT ABDOMEN W/ AND W/O CONTRAST SHOWS NO EVIDENCE     │
│ YANG MD, LIN       1 WEEK AGO    │ OF LIVER METASTISES OR OTHER ABNORMALITIES IN THE    │
│                                  │ ABDOMEN.                                             │
│ OP / PROCEDURE NOTES             │ PROCEDURE: ╱404                                      │
│ HAYDEN MD, SHILO   1 WEEK AGO    │ CONTRAST-ENHANCED AXIAL IMAGES WERE PERFORMED        │
│                                  │ THROUGH THE ABDOMEN.                                 │
│ NP OUTSIDE DOCUMENTS             │                                                      │
│ HAYDEN MD, SHILO   6 DAYS AGO    │ SIGNATURE LINE                                       │
│                                  │ *** FINAL ***                                    │
│ OUTSIDE LABORATORY TESTS         │                                                      │
│ HAYDEN MD, SHILO   6 DAYS AGO    │ SIGNED BY: HESLOP MD, RANDY                          │
│                                  │ SIGNED (ELECTRONIC SIGNATURE): 02/11/2013 11:20 AM   │
│ OUTSIDE RADIOLOGY TESTS          │ TRANSCRIBED BY: RH                                   │
│ YANG MD, LIN       1 WEEK AGO    │ TECHNOLOGIST                                         │
│                                  │                                                      │
│ OUTSIDE PATHOLOGY                │ TECHNICAL COMMENTS                                   │
│ HAYDEN MD, SHILO   1 WEEK AGO    │ TOTAL SCANNING TIME IN MINUTES? 10                   │
│                                  │                                                      │
│                                  │ THIS DOCUMENT HAS AN IMAGE                           │
└─────────────────────────────────┴──────────────────────────────────────────────────────┘

MENU - AMBULATORY

MEDICAL TREATMENT RECORD INTEGRATION

CROSS-REFERENCE TO RELATED APPLICATIONS

This application claims priority from U.S. Provisional Application No. 62/058,953, filed Oct. 2, 2014, entitled "Disease Diagnosis Record Integration", the entire contents of which are herein incorporated by reference.

This application is related by subject matter to concurrently filed U.S. patent application Ser. No. 14/585,488 and U.S. patent application Ser. No. 14/585,493, entitled "CANCER TREATMENT RECORD INTEGRATION" and "DISEASE DIAGNOSIS RECORD INTEGRATION," respectively, which are assigned or under obligation of assignment to the same entity as this application. The entirety of the aforementioned applications is incorporated by reference herein.

BACKGROUND

According to the World Health Organization (WHO), ischemic heart disease, stroke, lower respiratory infections, chronic obstructive lung disease, diarrheal diseases and HIV/AIDS have remained the top major killers worldwide during the past decade. Lung cancers, along with trachea and bronchus cancers, are also a major cause of death. For example, these cancers caused 1.5 million deaths globally in 2011. In general, cancer is considered a worldwide epidemic with 14.1 million adult diagnoses and 8.2 million adult deaths occurring in 2012. The WHO expects these numbers to climb dramatically over the next two decades. Estimates from the WHO suggest a rise from 14.1 million cancer cases annually to 22 million within the next 20 years. Furthermore, cancer deaths are expected to rise from 8.2 million to 13 million deaths per year. Cancer is not only deadly to the world's population; it is hitting the world's wallet at an estimated $1.16 trillion, just in the year 2010 alone.

With such a large portion of the world's population being diagnosed with cancer and other diseases, doctors require a reliable and efficient method for treating cancer and other diseases. One method that has recently been employed to treat patients is the use of decision trees. Decision trees are commonly used in decision analysis to help identify a strategy most likely to reach a goal. For example, cancer decision trees have recently been used by some medical facilities, such as the Moffitt Cancer Center. Decision trees allow for a step-by-step process in treating cancer and other diseases by allowing the physician to follow the specific symptoms of a particular patient and thereby tailor a specific treatment for that individual patient. However, the use of decision trees by physicians is accomplished by the physician manually following a specific decision tree. As the decision trees are utilized manually, there is room for improvement upon this approach. For example, integrating the specific decision tree for a patient into the patient's electronic medical record (EMR) can greatly aid physicians. The integration of the decision tree into the patient's EMR allows for an electronic approach to utilizing the decision tree. This integration also allows for a simpler approach to modifying or changing a particular decision tree, as needed, compared to the manual approach.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. The present invention is defined by the claims.

In one embodiment, there is a method in a medical information computing environment for suggesting a medical course of action for a cancer patient. In another embodiment, the patient is identified as having a cancer diagnosis. In yet another embodiment, an applicable cancer treatment decision tree based on the cancer diagnosis is identified. In a further embodiment, the cancer treatment decision tree is a series of branching nodes to determine a medical course of action for a cancer patient which may be satisfied by decision criteria, wherein the decision criteria comprises cancer patient questions, lab results, information derived from the patients electronic medical record (EMR), a physician's judgment, environmental factors, treatment toleration, and genetic factors. In another embodiment, the cancer treatment decision tree is integrated into an EMR of the cancer patient. In one embodiment, there is a processing of the series of branching nodes in the cancer treatment decision tree with the decision criteria for the patient until a node with a suggested medical course of action for the patient is satisfied. In another embodiment, there is exporting the suggested medical course of action for the cancer patient.

In one embodiment, there are branching nodes that contain one or more medications used to treat the cancer patient that also contain pricing information of the one or more medications. In another embodiment, the cancer treatment decision tree also comprises links to one or more periodicals or other forms of communication regarding the medical course of action for the cancer patient. In a further embodiment, the cancer treatment decision tree also comprises areas to make notes regarding the medical course of action for the cancer patient. In one embodiment, the cancer treatment decision tree also comprises warnings, precautions, toxicities, and side effects of a cancer patient's one or more medications. In yet another embodiment, one or more orders are placed at the branching nodes in the cancer treatment decision tree in order to satisfy the suggested medical course of action for the cancer patient. In an embodiment, there are one or more nodes in the cancer treatment decision tree that are satisfied by placing one or more orders to satisfy the suggested medical course of action for the cancer patient prior to reaching a final node within the cancer treatment decision tree. In another embodiment, lab results, tumor markers and diagnostics of the cancer patient are included in the cancer treatment decision tree. In a further embodiment, the cancer treatment decision tree comprises an initial workup section, a first line metastatic treatment section and a later line metastatic treatment section.

In one embodiment, there is a system in a medical information computing environment for suggesting a medical course of action for a cancer patient. In another embodiment, there is an identifying component for identifying a patient with a cancer diagnosis. In a further embodiment, there is an identifying component for identifying an applicable cancer treatment decision tree based on the cancer diagnosis, the cancer treatment decision tree being a series of branching nodes to determine a medical course of action for a cancer patient which may be satisfied by decision criteria, wherein the decision criteria comprises cancer patient questions, lab results, information derived from the patients EMR, a physician's judgment, environmental factors, treatment toleration, and genetic factors. In one embodiment, there is an integrating component for integrating the cancer treatment decision tree into an electronic medical record (EMR) of the cancer patient. In another embodiment, a processing component for processing the series of branching nodes in the cancer treatment decision tree with the decision criteria for the patient until a node with a suggested medical course of action for the patient is satisfied. In one embodiment, there is an exporting component for exporting the suggested medical course of action for the patient. In another embodiment, the exporting component is a graphical user interface (GUI).

In one embodiment, there are one or more computer-storage media having computer-executable instructions embodied thereon that, when executed, perform a method of integrating nodes of cancer treatment decision criteria to be satisfied into an electronic medical record (EMR) of a cancer patient. In another embodiment, there is receiving a cancer treatment decision tree from a third-party resource for a particular type of cancer diagnoses. In a further embodiment, there is creating nodes of cancer treatment decision criteria based on the cancer treatment decision tree for the cancer patient to be satisfied to determine a suggested medical course of action. In a further embodiment, there is integrating the nodes of the decision criteria into the EMR of the cancer patient. In one embodiment, there is processing the nodes of the decision criteria for the cancer patient for the suggested medical course of action. In another embodiment, there is receiving updates to the cancer treatment decision tree for the particular type of cancer diagnoses. In yet another embodiment, there is updating the nodes of the decision criteria for the cancer patient to be satisfied to determine a suggested medical course of action. In one embodiment, there is integrating the updated nodes of the decision criteria into the EMR of the cancer patient. In a further embodiment, there is processing the updated nodes of the decision criteria for the cancer patient for the suggested medical course of action.

In one embodiment, the nodes that contain one or more medications used to treat the cancer patient also contain pricing information of the one or more medications. In another embodiment, one or more nodes comprise links to one or more periodicals or other forms of communication regarding the suggested medical course of action for the cancer patient. In a further embodiment, one or more nodes comprise areas to make notes regarding the suggested medical course of action for the cancer patient. In yet another embodiment, one or more nodes comprise warnings, precautions, toxicities, and side effects of a cancer patient's medication. In one embodiment, one or more orders are placed at one or more nodes in order to satisfy the suggested medical course of action for the cancer patient. In another embodiment, there are one or more nodes that are satisfied by placing one or more orders to satisfy the suggested medical course of action for the cancer patient prior to reaching a final node. In a further embodiment, lab results, tumor markers and diagnostics of the cancer patient are included at one or more nodes. In one embodiment, the cancer treatment decision tree comprises an initial workup section, a first line metastatic treatment section and a later line metastatic treatment section.

In one embodiment, there is a method in a medical information computing environment for suggesting a medical course of action for a patient. In another embodiment, there is identifying for a patient a medical diagnosis. In a further embodiment, there is identifying an applicable medical treatment decision tree based on the medical diagnosis, the medical treatment decision tree being a series of branching nodes to determine a medical course of action for the patient which may be satisfied by decision criteria, wherein the decision criteria comprises patient questions, lab results, information derived from the patient's electronic medical record (EMR), a physician's judgment, environmental factors, treatment toleration, and genetic factors. In one embodiment, there is integrating the medical treatment decision tree into an EMR of the patient. In another embodiment, there is altering the applicable medical treatment decision tree or creating a new applicable medical treatment decision tree based on medical needs of the patient. In yet another embodiment, there is integrating the altered or new applicable medical treatment decision tree into the EMR of the patient. In one embodiment, there is processing the series of branching nodes in the medical treatment decision tree with the decision criteria for the patient until a node with a suggested medical course of action for the patient is satisfied. In another embodiment, there is exporting the suggested medical course of action for the patient.

In one embodiment, the branching nodes that contain one or more medications used to treat the patient also contain pricing information of the one or more medications. In another embodiment, the medical treatment decision tree also comprises links to one or more periodicals or other forms of communication regarding the medical course of action for the patient. In a further embodiment, the medical treatment decision tree also comprises areas to make notes regarding the medical course of action for the patient. In one embodiment, the medical treatment decision tree also comprises warnings, precautions, toxicities, and side effects of a patient's one or more medications. In another embodiment, one or more orders are placed at the branching nodes in the medical treatment decision tree in order to satisfy the suggested medical course of action for the patient. In one embodiment, there are one or more nodes in the medical treatment decision tree that are satisfied by placing one or more orders to satisfy the suggested medical course of action for the patient prior to reaching a final node within the medical treatment decision tree. In one embodiment, lab results and diagnostics of the patient are included in the medical treatment decision tree. In a further embodiment, the exporting is to a graphical user interface (GUI).

In one embodiment, there is a system in a medical information computing environment for suggesting a medical course of action for a patient. In another embodiment, there is an identifying component for identifying a patient with a medical diagnosis. In a further embodiment, there is an identifying component for identifying an applicable medical treatment decision tree based on the medical diagnosis, the medical treatment decision tree being a series of branching nodes to determine a medical course of action for the patient which may be satisfied by decision criteria, wherein the decision criteria comprises patient questions, lab results, information derived from the patient's electronic medical record (EMR), a physician's judgment, environmental factors, treatment toleration, and genetic factors. In one embodiment, there is an integrating component for integrating the medical treatment decision tree into an EMR of the patient. In another embodiment, there is an altering component for altering the applicable medical treatment decision tree or creating a new applicable medical treatment decision tree based on medical needs of the patient. In one embodiment, there is an integrating component for integrating the altered or new applicable medical treatment decision tree into the EMR of the patient. In another embodiment, there is a processing component for processing the series of branching nodes in the medical treatment decision tree with the decision criteria for the patient until a node with a suggested medical course of action for the patient is satisfied. In a further embodiment, there is an exporting component for exporting the suggested medical course of action for the patient. In one embodiment, the exporting component is a graphical user interface (GUI).

In one embodiment, there are one or more computer-storage media having computer-executable instructions embodied thereon that, when executed, perform a method of integrating nodes of disease treatment decision criteria to be satisfied into an electronic medical record (EMR) of a patient. In another embodiment, there is receiving a disease treatment decision tree from a third-party resource for a particular type of disease diagnoses. In one embodiment, there is creating nodes of disease treatment decision criteria based on the disease treatment decision tree for the patient to be satisfied to determine a suggested medical course of action. In a further embodiment, there is integrating the nodes of the decision criteria into the EMR of the patient. In another embodiment, there is processing the nodes of the decision criteria for the patient for the suggested medical course of action. In one embodiment, there is receiving updates to the disease treatment decision tree for the particular type of disease diagnoses. In another embodiment, there is altering or creating new nodes of the decision criteria for the patient to be satisfied based on medical needs of the patient. In yet another embodiment, there is integrating the altered or new nodes of the decision criteria for the patient to be satisfied into the EMR of the patient. In one embodiment, there is processing the updated nodes of the decision criteria for the patient for the suggested medical course of action.

In one embodiment, the nodes that contain one or more medications used to treat the patient also contain pricing information of the one or more medications. In another embodiment, one or more nodes comprise links to one or more periodicals or other forms of communication regarding the suggested medical course of action for the patient. In yet another embodiment, one or more nodes comprise areas to make notes regarding the suggested medical course of action for the patient. In one embodiment, one or more nodes comprise warnings, precautions, toxicities, and side effects of a patient's medication. In a further embodiment, one or more orders are placed at one or more nodes in order to satisfy the suggested medical course of action for the patient. In one embodiment, there are one or more nodes that are satisfied by placing one or more orders to satisfy the suggested medical course of action for the patient prior to reaching a final node. In another embodiment, lab results and diagnostics of the patient are included at one or more nodes. In a further embodiment, pathology results, vitals and measurements of the patient are included at the one or more nodes.

In one embodiment, there is ordering a medical procedure based on the suggested medical course of action for the patient. In another embodiment, there is integrating the medical procedure into the medical treatment decision tree located in the EMR of the patient. In a further embodiment, there is documenting that the medical procedure was ordered in the treatment decision tree located in the EMR of the patient.

In one embodiment, there is an ordering component for ordering a medical procedure based on the suggested medical course of action for the patient. In another embodiment, there is an integrating component for integrating the medical procedure into the medical treatment decision tree located in the EMR of the patient. In yet another embodiment, there is a documenting component for documenting that the medical procedure was ordered in the treatment decision tree located in the EMR of the patient.

In one embodiment, there is updating the nodes of the decision criteria for the patient to be satisfied to determine a suggested medical course of action. In another embodiment, there is integrating the updated nodes of the decision criteria into the EMR of the patient. In one embodiment, there is integrating the medical procedure into the updated nodes of the decision criteria in the EMR of the patient. In another embodiment, there is documenting that the medical procedure was ordered in the updated nodes of the decision criteria in the EMR of the patient.

BRIEF DESCRIPTION OF THE SEVERAL VIEWS OF THE DRAWINGS

FIGS. 3A-7 are exemplary graphical user interfaces illustrating the presentation of actionable content items related to the integration of a disease decision tree into the patient's EMR in accordance with embodiments of the present invention.

DETAILED DESCRIPTION

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
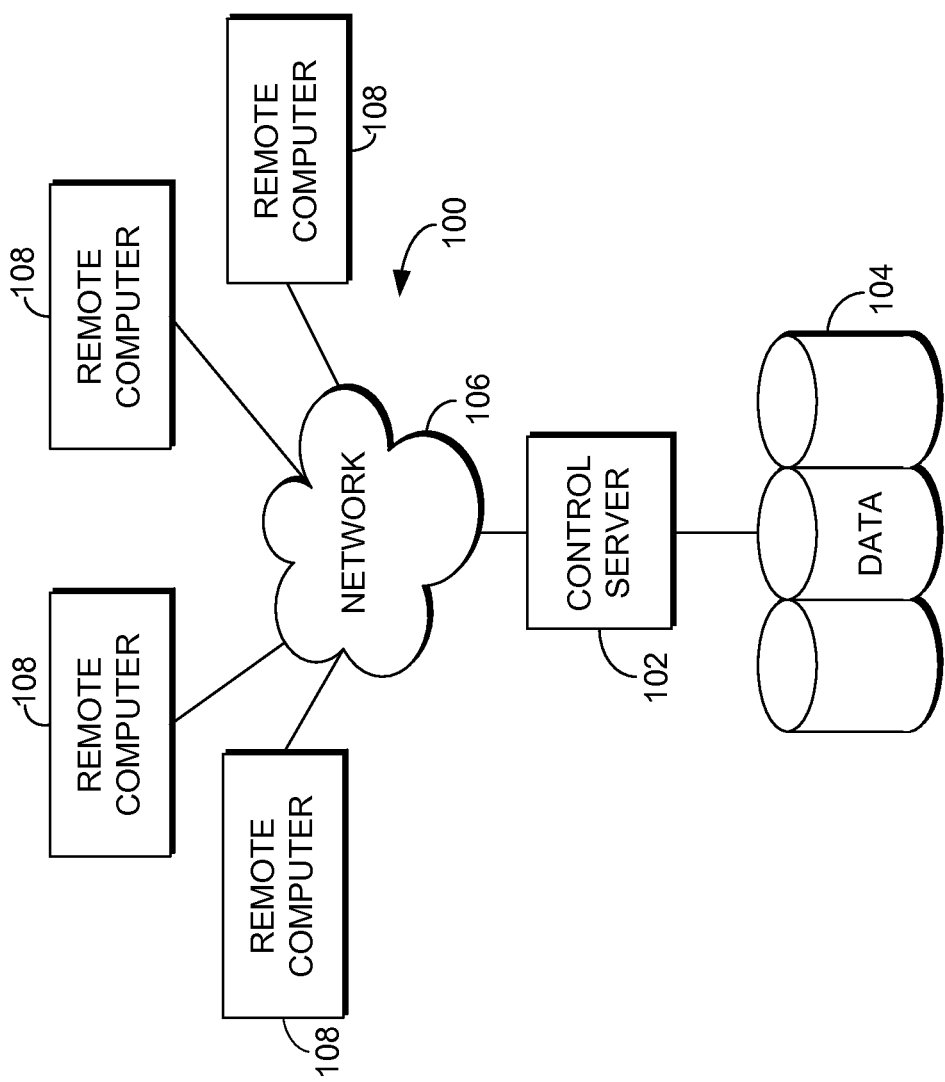
FIG. 1 is a schematic diagram of a suitable computing system environment for use in implementing the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2A:
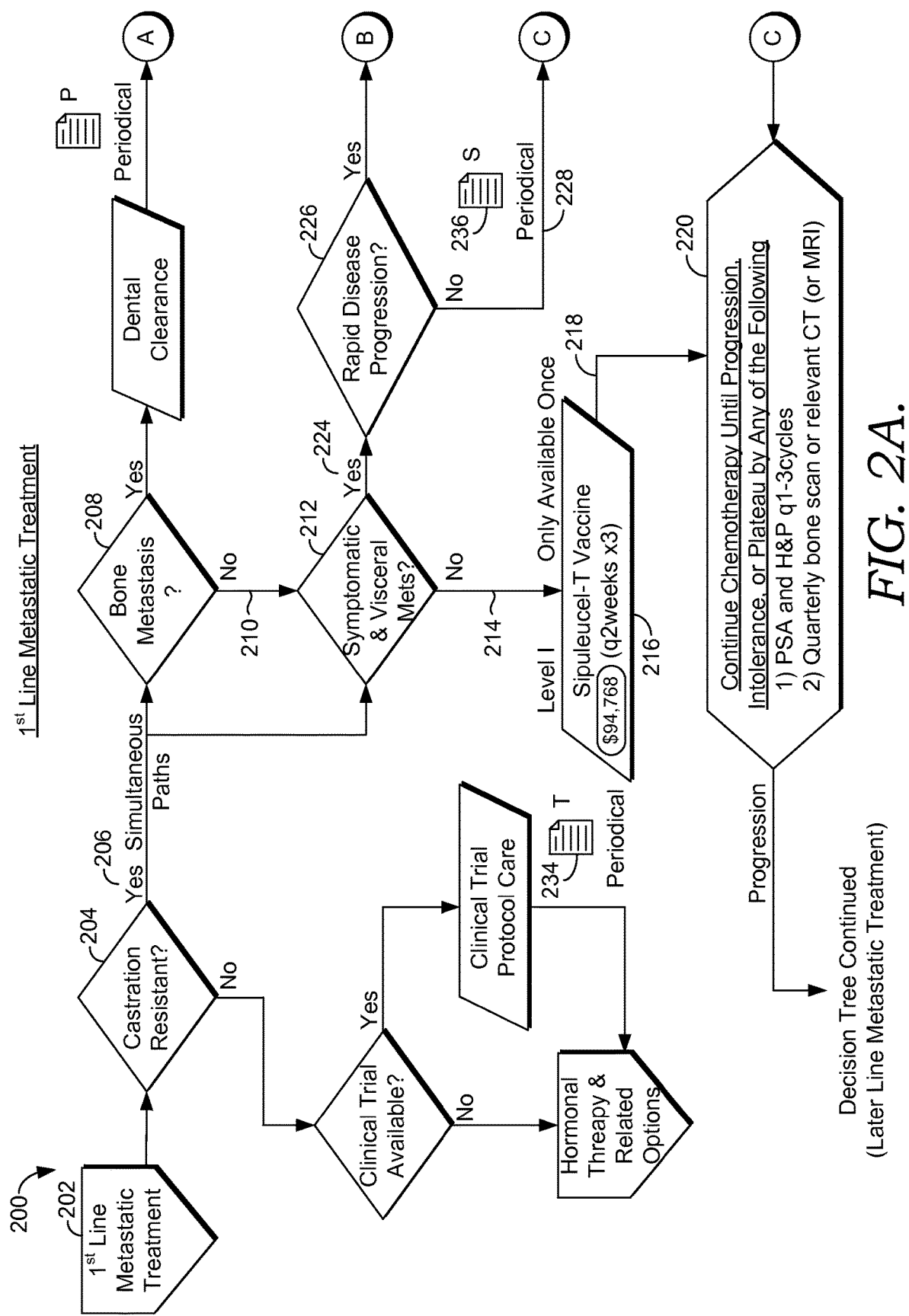
FIGS. 2A-2B depict a schematic diagram of a portion of a decision tree for first line metastatic treatment of prostate adenocarcinoma.
Figure 2B:
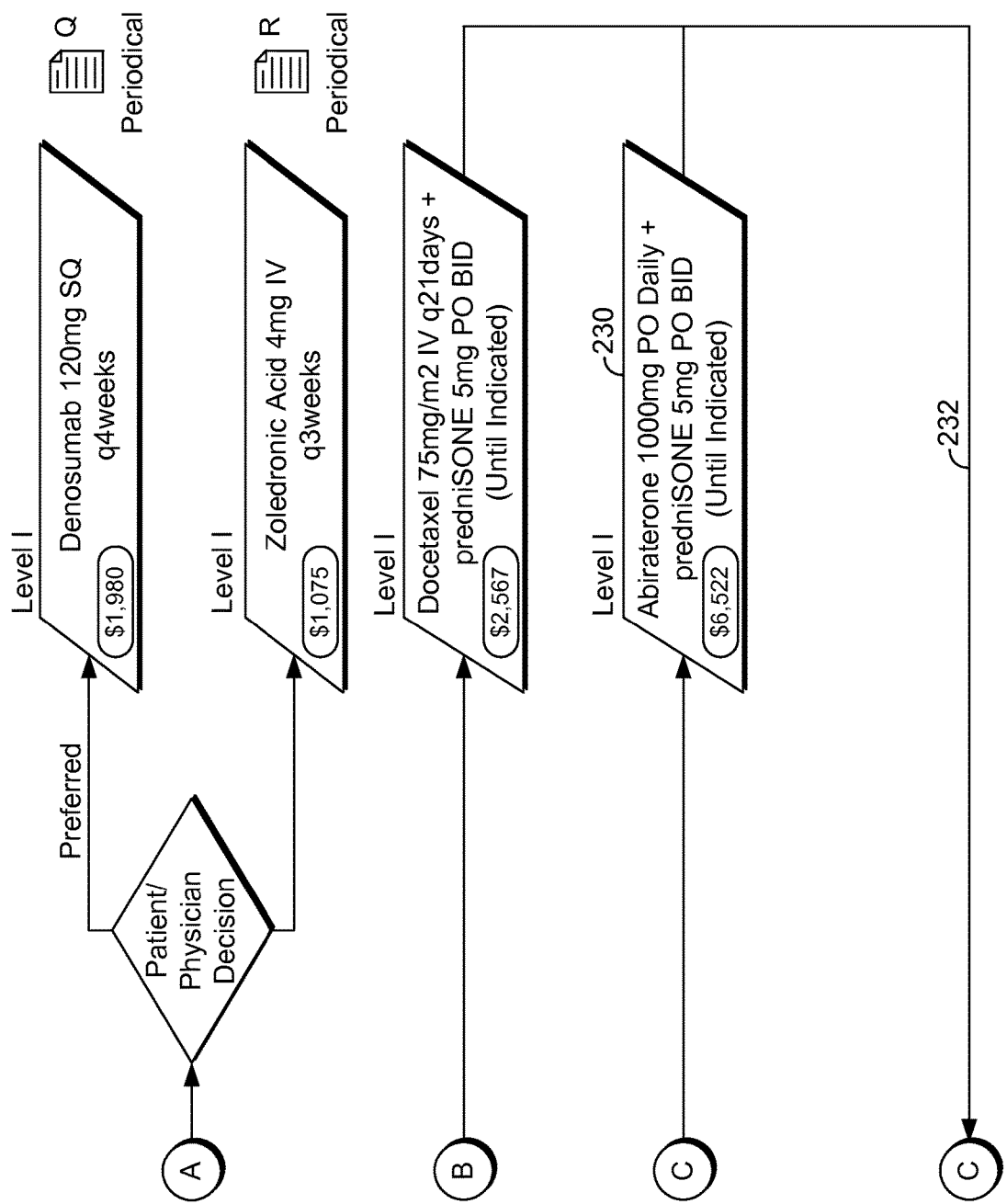

Turning now to FIG. 2, illustrated is a portion of a decision tree, or pathway. The decision tree illustrated in FIG. 2 was developed by Moffitt Cancer Center and is merely an exemplary decision tree or pathway that may be integrated into the system and method of the present invention. Illustrated is the first line metastatic treatment for prostate adenocarcinoma 200. The starting node, or root node, illustrates that this decision tree is the first line metastatic treatment 202 of prostate adenocarcinoma (not shown). The remaining nodes are referred to as branching nodes, which are made up of leaf nodes and answer nodes.

The first leaf node of the branching nodes asks the question if the cancer is castration resistant 204. Castration resistance simply refers to cancer cells that are resistant to hormonal treatment. For illustration purposes only, if the prostate adenocarcinoma is castration resistant, then the "Yes" branch 206 is followed to its corresponding leaf node(s). In this case, the "Yes" branch 206 has two simultaneous paths. These two paths lead to two different leaf nodes. One node asks the question if bone metastasis has occurred 208. The other node asks the question if symptomatic and visceral metastases has occurred 212. For illustration purposes only, if the adenocarcinoma has not metastasized to the bone, then the "No" branch 210 is followed to the leaf node that asks the question if symptomatic and visceral metastases has occurred 212. Again, for illustration purposes only, if there is no symptomatic and visceral metastases, then the "No" branch 214 is followed to an answer node 216. In this case, the answer node indicates that Sipuleucel-T vaccine is to be given to the cancer patient every two weeks for a total of three times 216. Following branch 218 to the next answer node 220 indicates that chemotherapy is to continue until progression, intolerance, or plateau as indicated by the following: 1) prostate-specific antigen (PSA) count and a history and physical, which are to be conducted every one to three cycles of chemotherapy and/or 2) quarterly bone scan, relevant computed tomography (CT) scan or magnetic resonance imaging (MRI). In this particular example, if there is progression of the cancer, then the progression branch 222 is followed to the later line metastatic treatment portion of the decision tree (not shown). For illustration purposes only, if the cancer patient is symptomatic and showing visceral metastases at leaf node 212, then the "Yes" branch 224 is followed to a leaf node 226. This leaf node asks the question if there is a rapid disease progression 226. If the answer is no, then the "No" branch 228 is followed to the answer node 230. Answer node 230 indicates that the patient is to be given Abiraterone at 1000 mg by mouth daily and predniSONE at 5 mg by mouth twice daily until indicated. Following branch 232 to the next answer node 220 indicates that chemotherapy is to continue until progression, intolerance, or plateau as indicated by the following: 1) prostate-specific antigen (PSA) count and a history and physical, which are to be conducted every one to three cycles of chemotherapy and/or 2) quarterly bone scan, relevant computed tomography (CT) scan or magnetic resonance imaging (MRI). In this particular example, if there is progression of the cancer, then the progression branch 222 is followed to the later line metastatic treatment portion of the decision tree (not shown).

With continued reference to FIG. 2, decision trees of this invention do not have to be cancer specific and may represent any disease. Furthermore, the decision trees are dynamic, in the sense that they can be updated or changed. Additionally, periodicals or other forms of communication regarding a particular step or node within the decision tree can be represented by an icon. For example, periodical T at 234 represents the most current information regarding Sipuleucel-T vaccine and its role in cancer treatment. As another example, periodical S at 236 represents the most current information regarding Abiraterone and/or predniSONE and their role in cancer treatment. Periodicals or other forms of communication can be updated or added to a decision tree at any time to keep the decision tree as current as possible regarding cancer or disease treatment. In one embodiment, the periodical or other form of communication icon may be clickable, which will then open up the file to that particular periodical or other form of communication. What is meant by clickable is that the periodical or other form of communication can be opened by placing the mouse cursor over the icon and clicking it, by touching the icon when using a touch-screen monitor, or through other ways of opening the file that is represented by the icon.

Figure 3A:
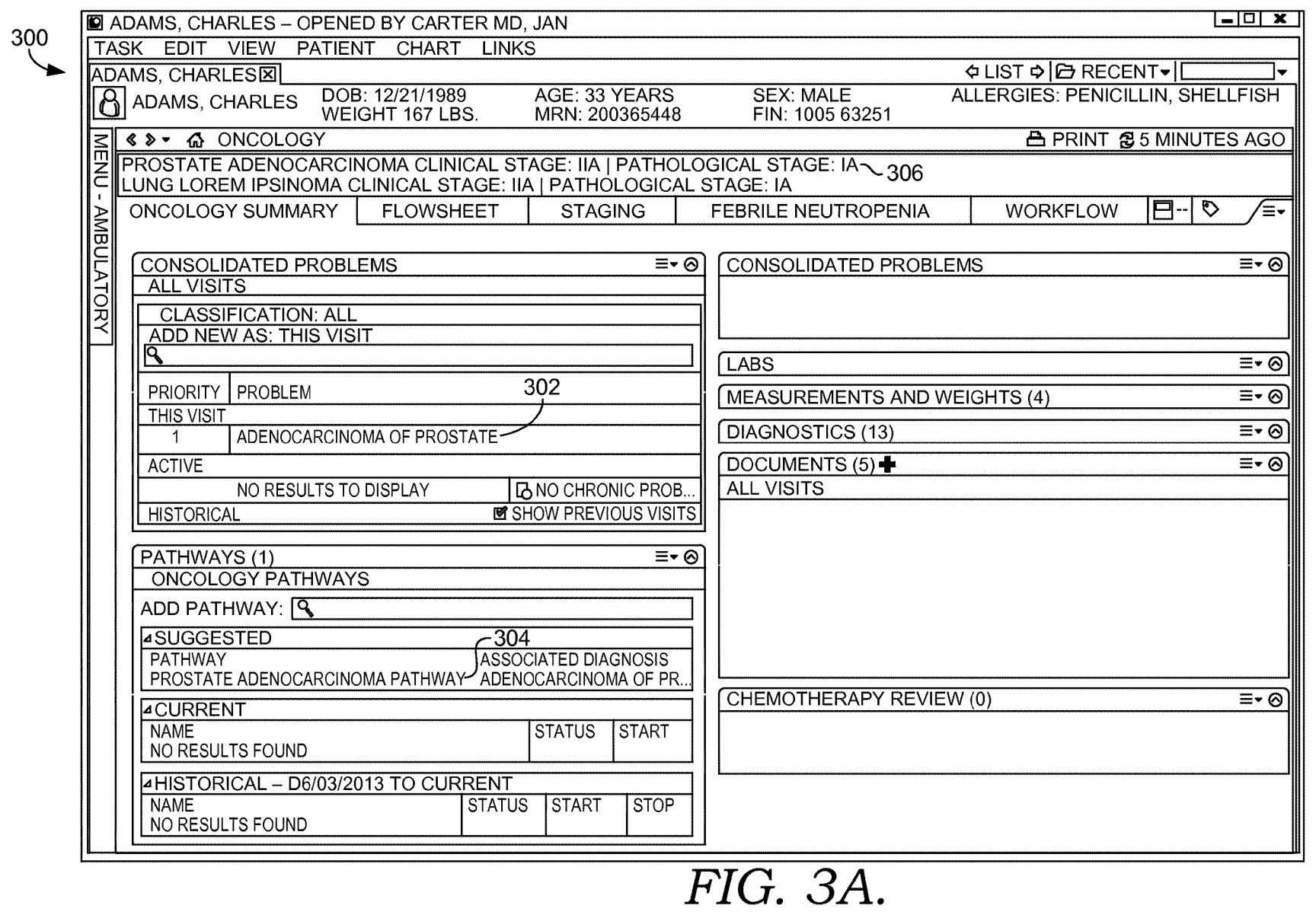
Figure 3B:

One advantage of the current invention is that decision trees can be integrated into the patient's electronic medical record (EMR). Turning now to FIG. 3A, illustrated is an EMR of the fictional patient Charles Adams 300. Within Charles Adam's EMR it indicates that he was diagnosed with prostate adenocarcinoma on the current visit 302. Under the heading "Suggested", the prostate adenocarcinoma pathway, or decision tree, is suggested for treatment of the patient 304. It is also indicated towards the top of the EMR that the patient is in clinical stage IIA and pathological stage IA 306. Turning now to FIG. 3B, it is noted that upon the patient's initial workup, it was found that the patient has greater than five years of non-prostate cancer life expectancy 308. It is also noted that the prostate cancer tumor size is T3-4, the patient is symptomatic and presents with evidence of clinical metastasis 308. As illustrated in FIG. 3B, the first line metastatic treatment "Start" button is clicked in order to start the applicable pathway, or decision tree 310. Note that this is after the patient has been diagnosed. Decision trees may also exist that aid physicians in diagnosing patients with the patient's initial workup. In fact, decision trees may exist at any step during the treatment of a patient.

Figure 4B:
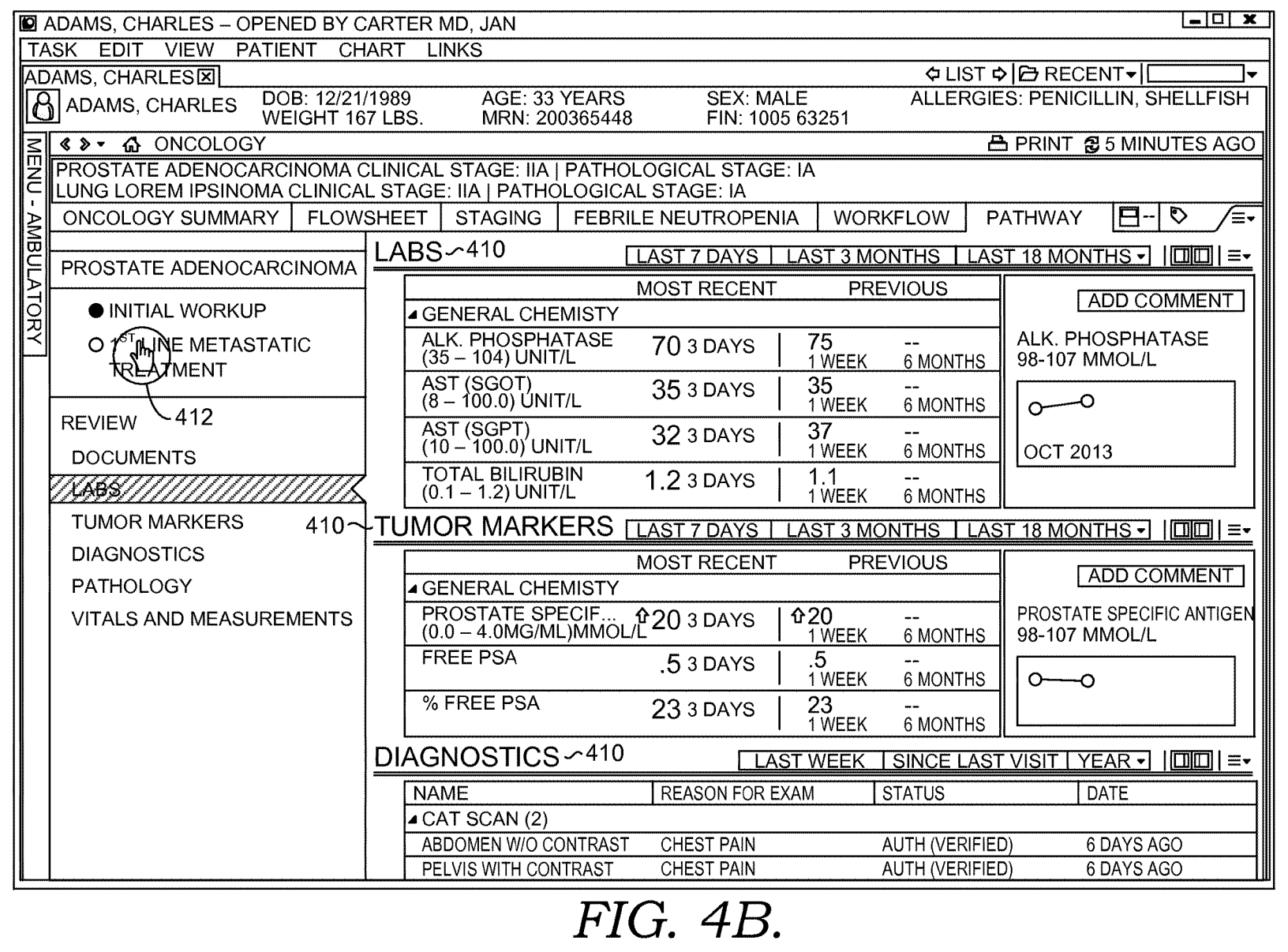

Turning to FIG. 4A, illustrated is the patient's EMR, wherein the patient's documents from the initial workup decision tree or pathway have been integrated into the EMR of the patient 400. Shaded is a CT abdomen without contrast that was conducted six days ago and ordered by Shilo Hayden, M.D. 402. The final report in this example shows the reason for the exam, the impression of the results, and the procedure itself 404. In this example, the impression indicates no evidence of liver metastasis or other abnormalities in the abdomen 406. As indicated by the cursor, the next section to be examined is the "Labs" section of the initial workup decision tree or pathway 408. As illustrated in FIG. 4B, the labs indicated are general chemistry labs, tumor markers and diagnostics 410. In this particular example, the next step is to move to the first line metastatic treatment section decision tree or pathway, as indicated by the cursor 412.

Figure 5A:
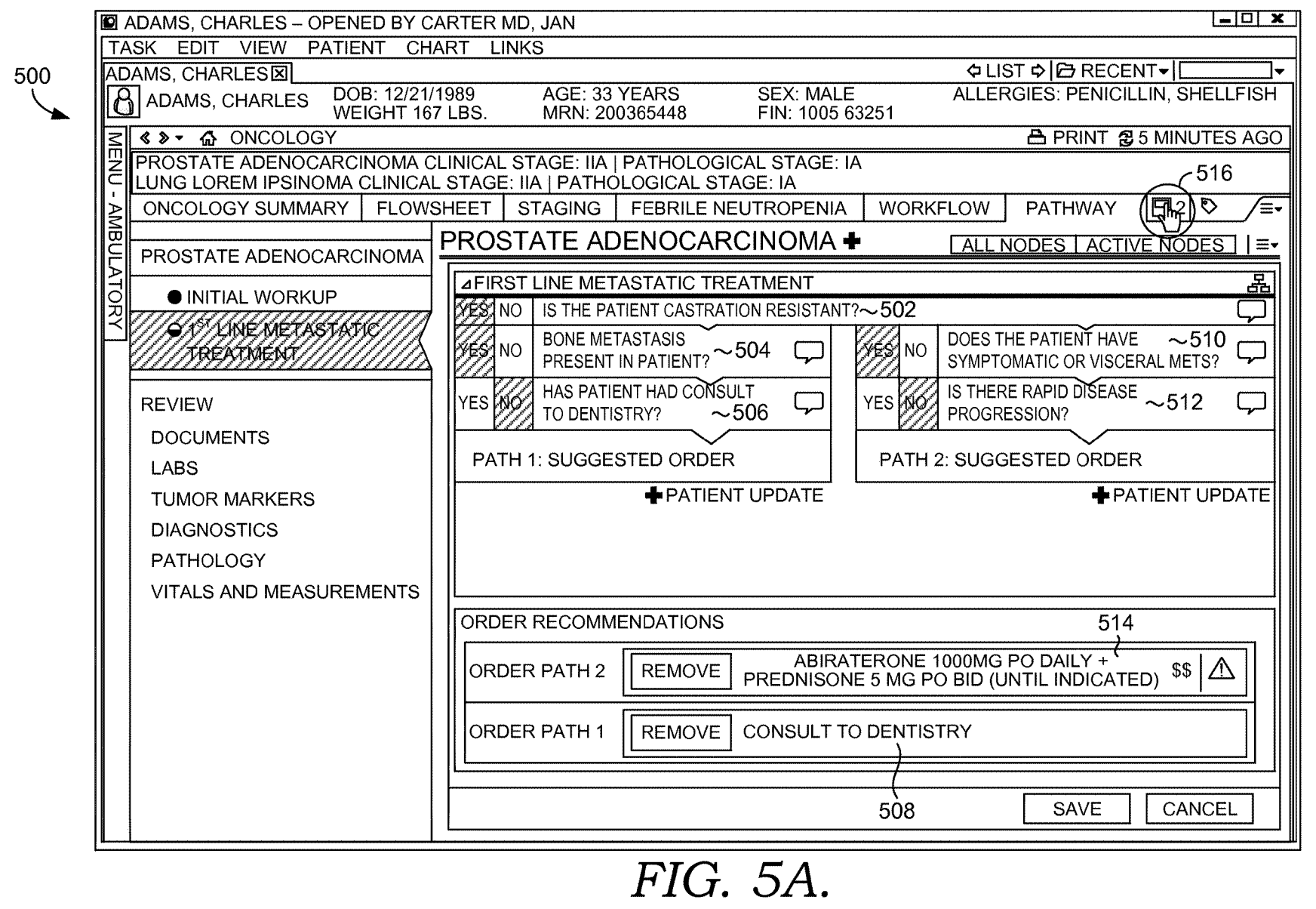
Figure 5B:
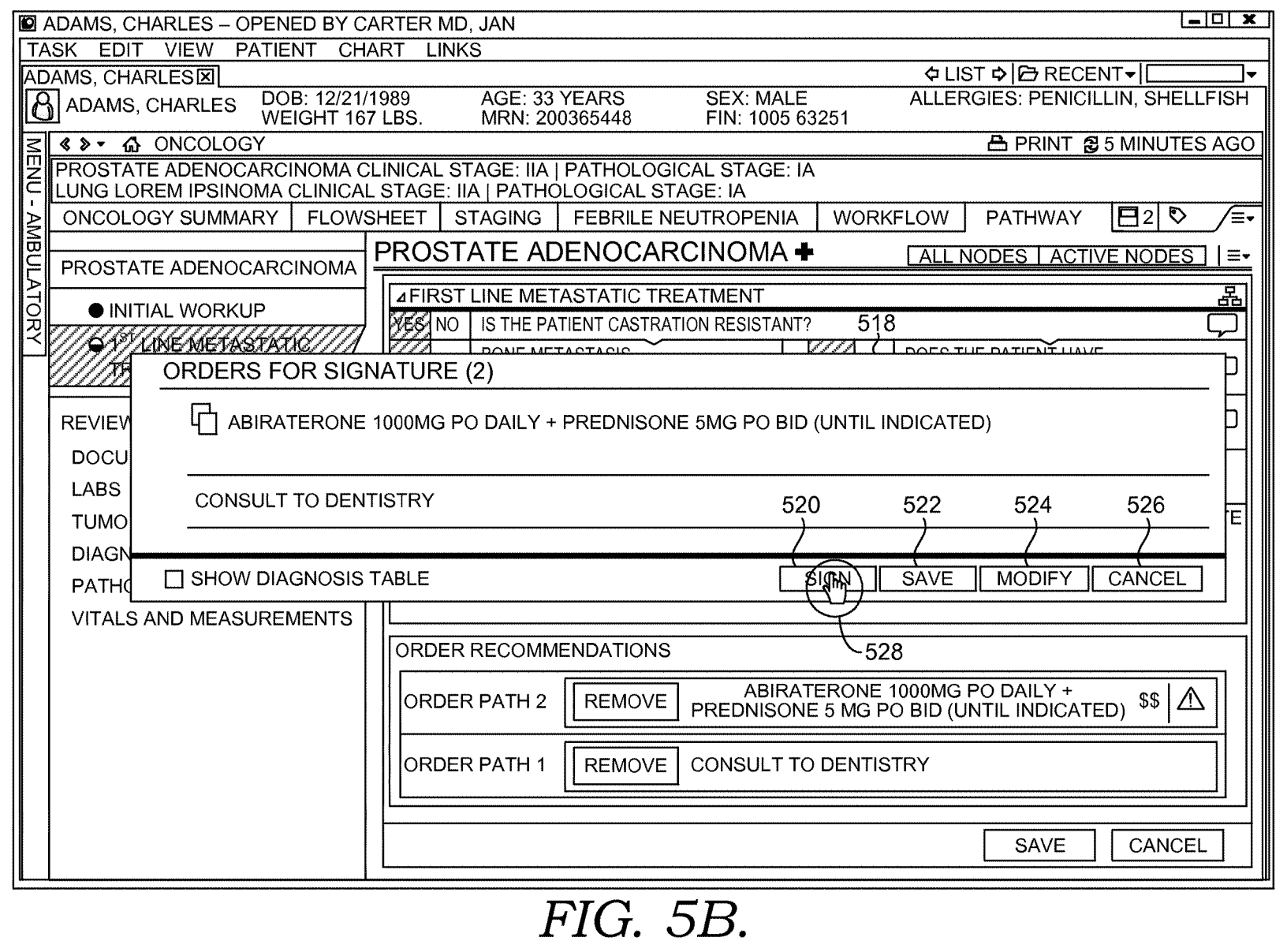
Figure 5C:
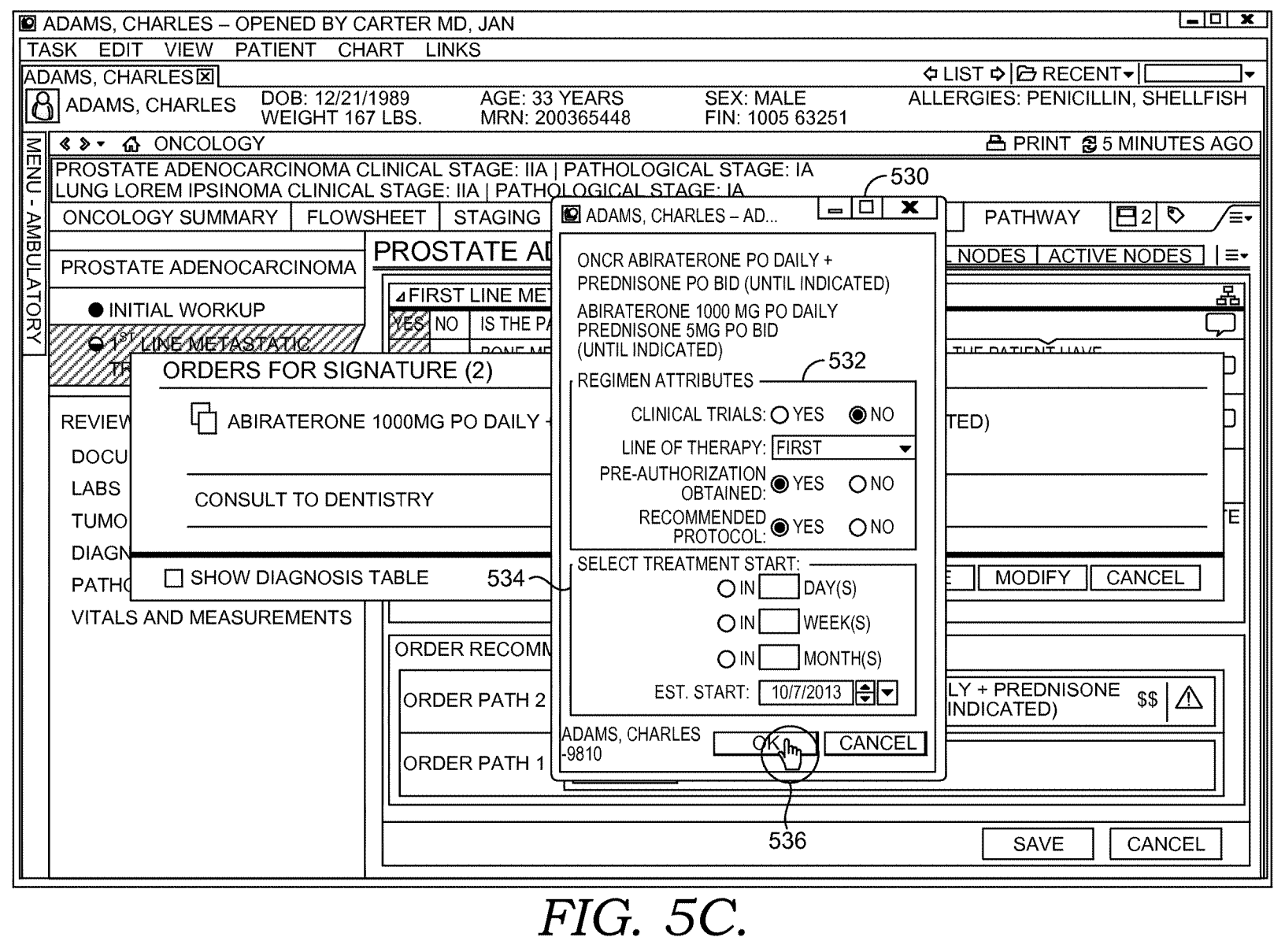
Figure 5D:
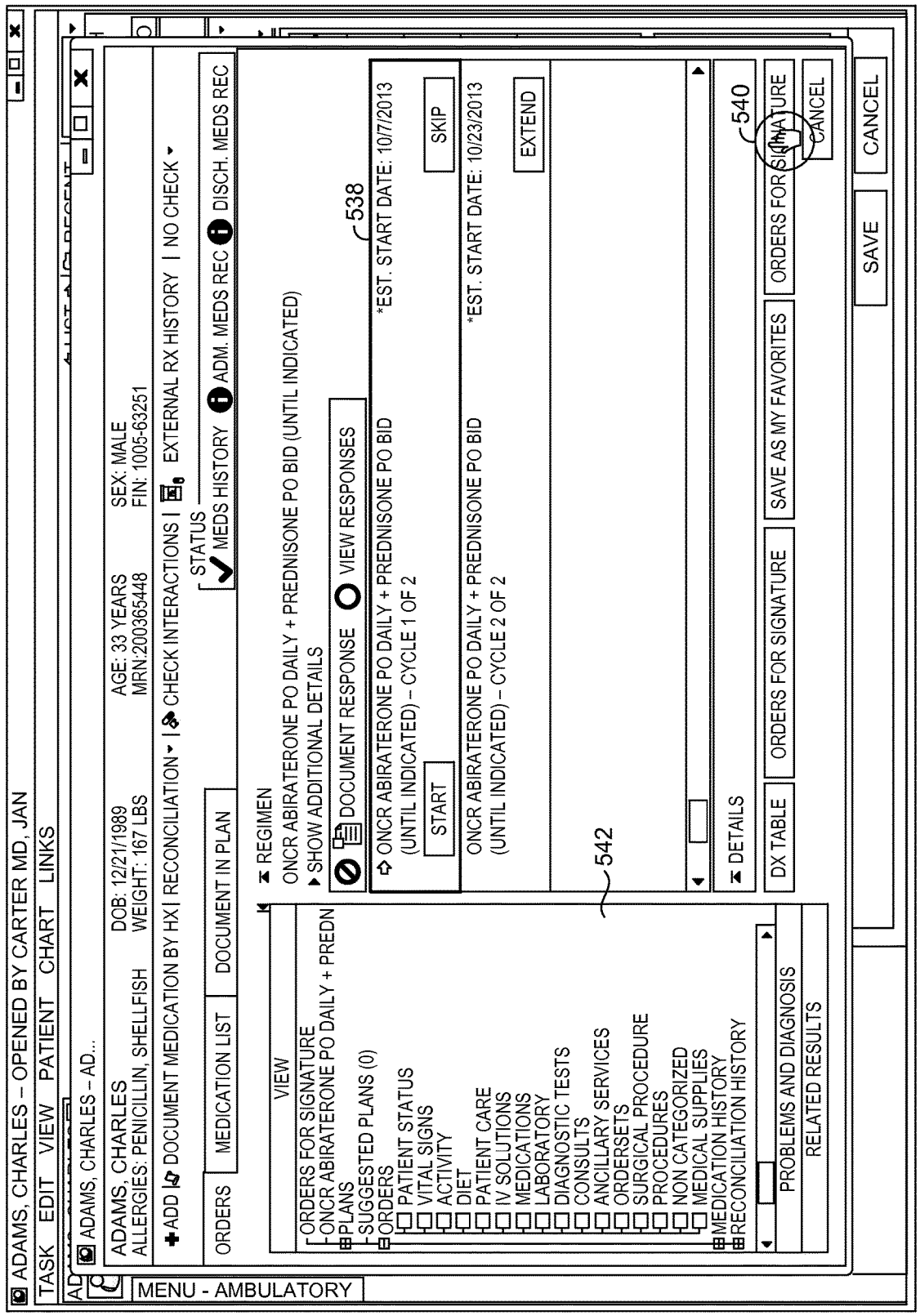

Turning now to FIG. 5A, illustrated is the patient's EMR, wherein the first line metastatic treatment for prostate adenocarcinoma decision tree, or pathway, has been integrated into the EMR of the patient 500. In this example, the decision tree of FIG. 2 is followed electronically through the patient's EMR. As indicated in the patient's EMR, the patient is castration resistant 502, which leads to branch 206 that leads to two simultaneous paths. One path asks the question if bone metastasis has occurred 208. In this particular example, bone metastasis has occurred in the patient 504. Following the "Yes" branch to the next leaf node in FIG. 2 indicates that the patient requires dental clearance. However, in this example, the patient has not undergone a dentistry consult 506. Thus, for order path 1, a consult to dentistry is ordered 508. Following path 2, the question is asked whether the patient has symptomatic and visceral metastases 212. In this particular example, the patient does have symptomatic and visceral metastases 510. Therefore, branch 224 is followed to the leaf node 226, which asks the question if there is rapid disease progression. In this example, there is no rapid disease progression 512. Therefore, branch 228 is followed to the answer node 230, which indicates that the patient is to be given Abiraterone at 1000 mg by mouth daily and predniSONE at 5 mg by mouth twice daily until indicated. Thus, since the decision tree is integrated into the EMR of the patient, the EMR recommends giving the patient Abiraterone at 1000 mg by mouth daily and predniSONE at 5 mg by mouth twice daily until indicated for order path 2 514. As indicated by the cursor 516, there are now two suggested orders awaiting signing by a physician or whomever is in charge of signing the orders. Turning now to FIG. 5B, once the icon is clicked or the cursor hovers over the icon 516, then a pop-up screen appears that shows the two suggested orders 518. The physician then has an opportunity to sign 520, save 522, modify 524 and/or cancel 526 the order. Both orders can be signed 520, saved 522, modified 524 and/or cancelled 526 at the same time or separately. In this example, the orders are signed, as illustrated by the cursor 528. Turning to FIG. 5C, illustrated is a second pop-up window that allows for the addition of the medical regimen 530. Included within the medical regimen pop-up window 530 are the regimen attributes 532 and the treatment start time 534. The regimen can either be cancelled by clicking the "Cancel" button or accepted by clicking the "OK" button, as illustrated by the cursor 536 in this example. Turning now to FIG. 5D, illustrated is the order details. Thus, after clicking the "OK" button 536, the details of the orders appear in a new pop-up window. Highlighted is cycle 1 of 2 of the medications to be given to the patient 538. Once the applicable section is highlighted, the "Orders for Signature" can be clicked, as indicated by the cursor in this example 540. Located in the left pane 542 of the new pop-up window is a view of the "Orders for Signature", "Plans", "Orders", "Medication History", "Reconciliation History", and the like.

Figure 6A:
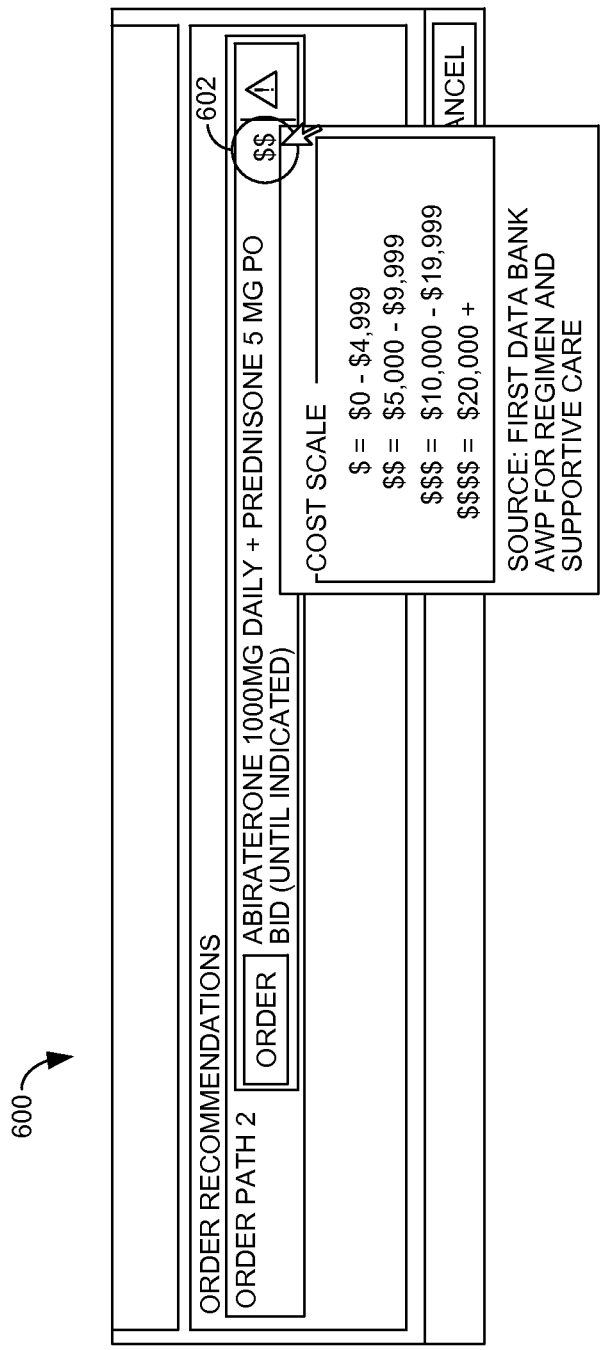
Figure 6B:
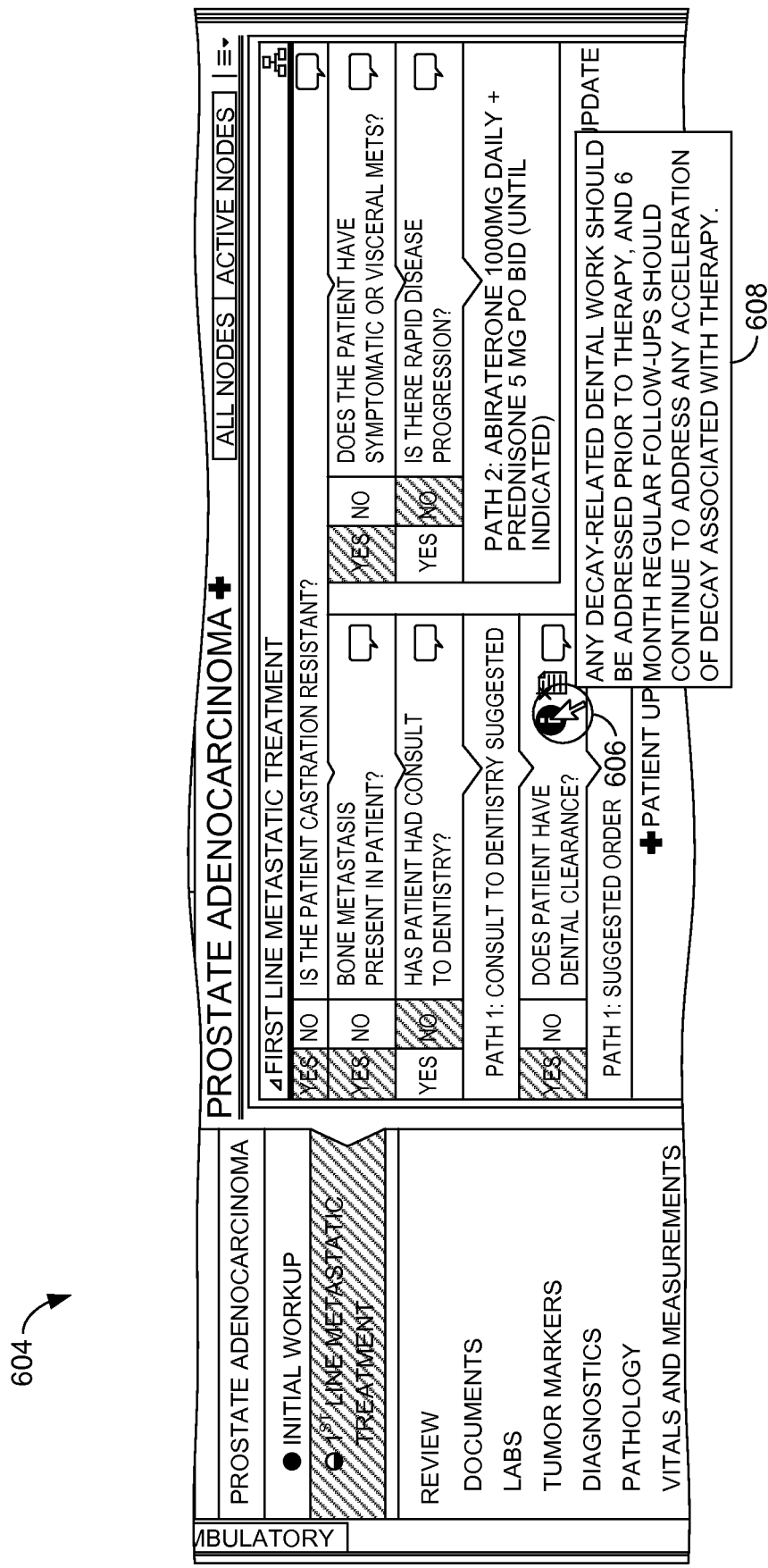
Figure 6C:
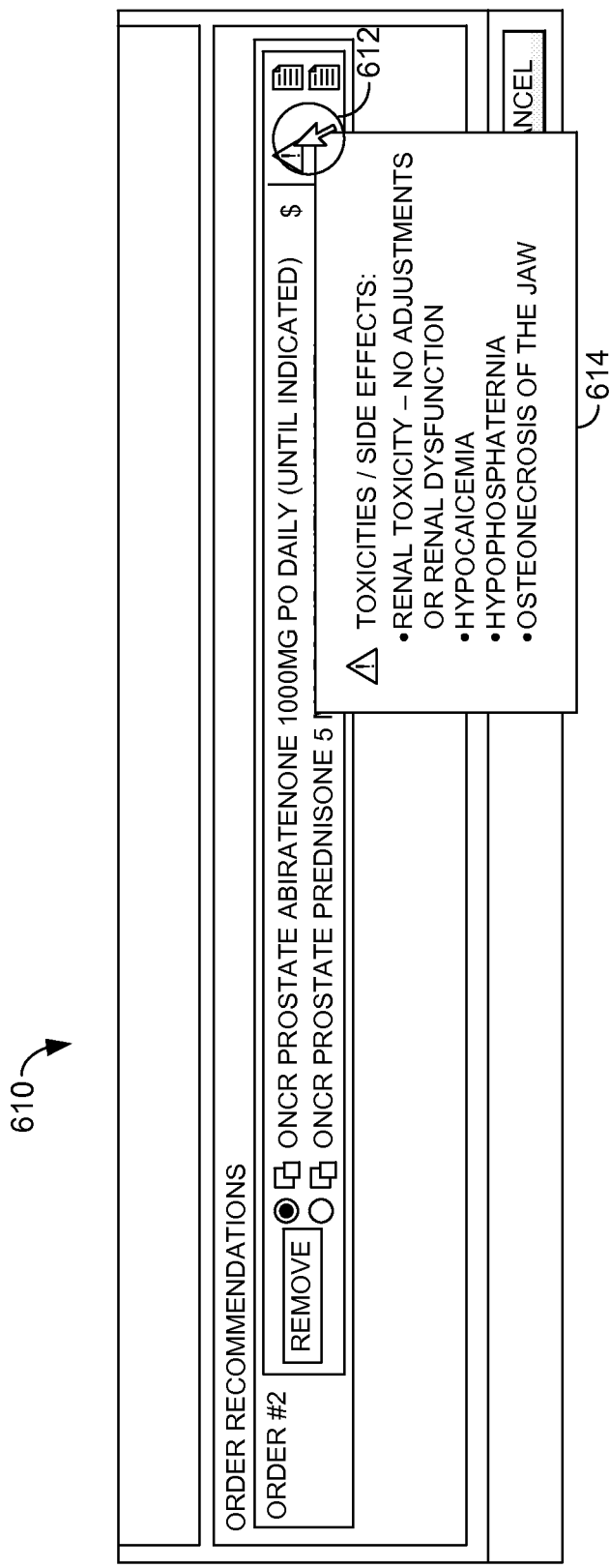

Turning to FIG. 6A, illustrated is the "Order Recommendations" section of the EMR 600. A cost estimate of the particular medication(s) is available as indicated by the cursor 602. This particular cost estimate is for illustration purposes only and can be changed and/or modified as needed. Turning now to FIG. 6B, illustrated is the first line metastatic treatment decision tree as displayed within the EMR of the patient 604. As indicated by cursor 606, information about a particular step of the decision tree can be available to aid the user. For example, as cursor 606 hovers over the information button, or clicks the information button, a pop-up window displays information regarding that particular step in the decision tree 608. Turning to FIG. 6C, illustrated is the "Order Recommendations" section of the EMR 610. Warnings, precautions, toxicities, and/or side effects of a given medication is available as indicated by the cursor 612. This particular warning box 614 is for illustration purposes only and each medication will have its own warning box.

Figure 7:
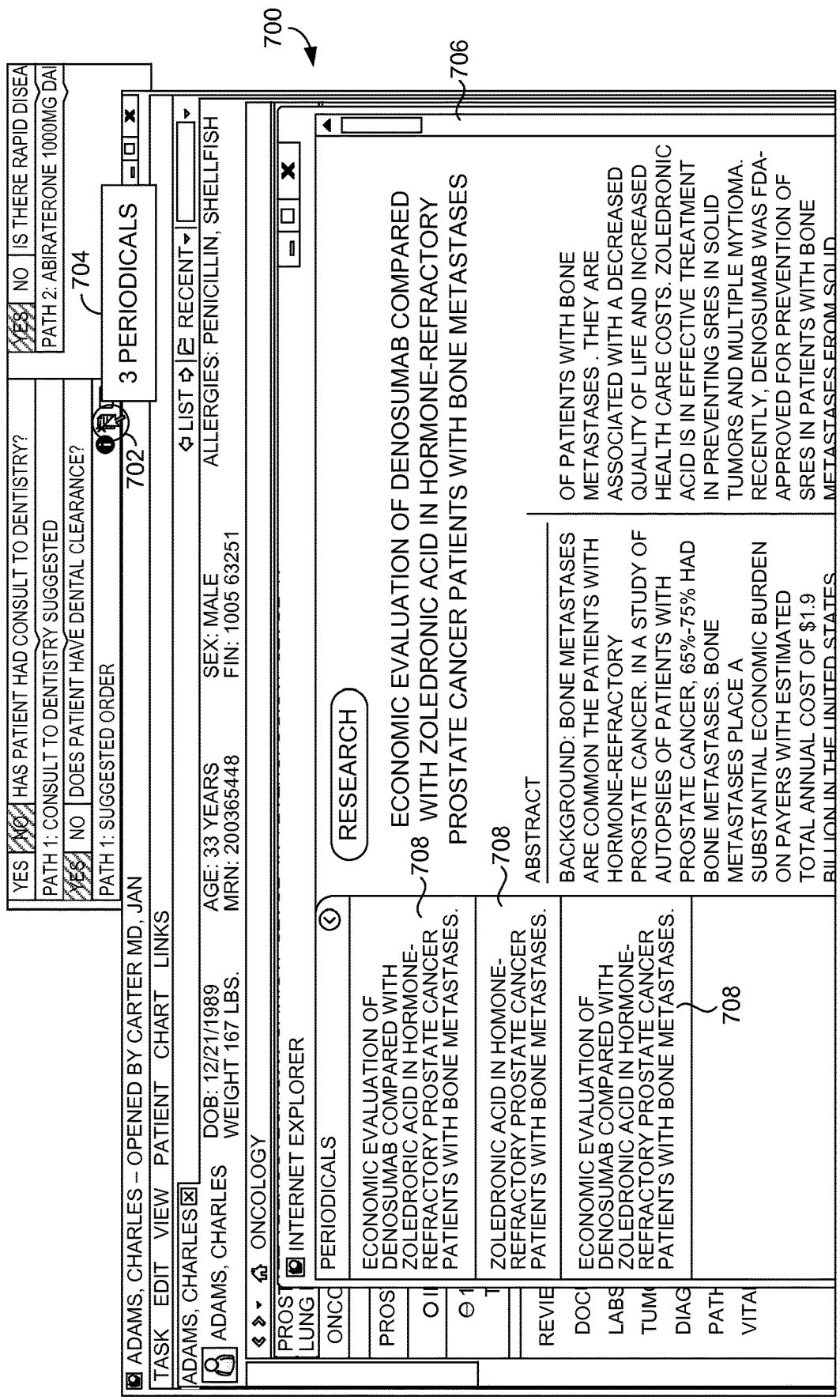

Turning now to FIG. 7, illustrated is the first line metastatic treatment decision tree as displayed within the EMR of the patient 700. As indicated by cursor 702, there are three periodicals regarding this particular step of the decision tree, which are available to aid the user. For example, as cursor 702 hovers over the periodical button, or clicks the periodical button, a pop-up window displays that there are three periodicals available 704. Upon hovering over the periodical button, or clicking the periodical button, another pop-up window 706 displays the three periodicals 708; making the three periodicals available for reading by the user. These periodicals are for illustration purposes only. Furthermore, the periodical button can also bring up other forms of communications besides periodicals, such as abstracts, books, newspaper articles, and the like. These periodicals or other forms of communication can be updated such that only the most current information regarding the particular step of the decision tree is available.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A method in a medical information computing environment for suggesting a medical course of action for a patient, the method comprising:

identifying an applicable medical treatment decision tree based on a medical diagnosis of a patient, the medical treatment decision tree being a series of branching nodes, each node having one or more medical courses of action for the patient;

integrating the medical treatment decision tree into an electronic medical record (EMR) of the patient;

providing pricing information for at least one node of the series of branching nodes;

causing for display on a graphical user interface of a computing device a plurality of clickable icons, each clickable icon of the plurality of clickable icons representing a communication of a set of communications associated with information related to a medical course of action for a node of the series of branching nodes, the set of communications comprising one or more communications;

automatically determining there is updated information related to the medical course of action for the node;

automatically updating the set of communications so that the updated information for the node is included in the set of communications;

processing the series of branching nodes in the medical treatment decision tree;

ordering a medical procedure based on the medical course of action at the node; and integrating results of the medical procedure into the medical treatment decision tree located in the EMR of the patient.

2. The method of claim 1, wherein the medical treatment decision tree also comprises areas to make notes regarding the medical course of action for the patient.

3. The method of claim 1, wherein one or more nodes of the series of branching nodes comprises warnings, precautions, toxicities, and side effects of one or more medications associate with the one or more nodes.

4. The method of claim 1, wherein one or more orders are placed at one or more nodes of the series of branching nodes in the medical treatment decision tree in order to satisfy the suggested medical course of action for the one or more nodes.

5. The method of claim 1, wherein there are one or more nodes in the medical treatment decision tree that are satisfied by placing one or more orders to satisfy the suggested medical course of action for the patient prior to reaching a final node within the medical treatment decision tree.

6. The method of claim 1, wherein lab results and diagnostics of the patient are included in the medical treatment decision tree.

7. A system in a medical information computing environment for suggesting a medical course of action for a patient, the system comprising:

one or more hardware processors having computer-executable instructions stored thereon which, when executed by the hardware processors, implement a method of suggesting a medical course of action for a patient, the method comprising:

identifying an applicable medical treatment decision tree based on a medical diagnosis for the patient, the medical treatment decision tree being a series of branching nodes to determine a medical course of action for the patient which may be satisfied by decision criteria;

integrating the medical treatment decision tree into an electronic medical record (EMR) of the patient, wherein at least one node of the series of branching nodes contains pricing information;

communicating for display on a graphical user interface of a computing device at least a portion of the medical treatment decision tree, the at least one node included in the portion of the medical treatment decision tree communicated for display, and for communicating for display the pricing information for the at least one node, wherein the pricing information for the at least one node is displayed adjacent to the at least one node;

processing the series of branching nodes in the medical treatment decision tree with the decision criteria for the patient until a node with a suggested medical course of action for the patient is satisfied;

adding a set of communications to one or more nodes of the series of branching nodes, the set of communications having information associated with the suggested medical course of action, wherein each communication of the set of communications is one of a periodical, an abstract, a book, or a newspaper article;

causing for display on a graphical user interface of a computing device a plurality of clickable icons, each clickable icon of the plurality of clickable icons representing a communication of the set of communications associated with information related to a medical course of action for the node of the series of branching nodes, the set of communications comprising one or more communications;

automatically updating at least one communication of the set of communications or adding a new communication to the set of communication, the update or the new communication having updated information regarding the suggested medical treatment associated with the node, wherein based on the updated information regarding the suggested medical treatment, the update component dynamically alters the decision tree; and ordering a medical procedure based on the suggested medical course of action for the patient.

8. One or more non-transitory computer-storage media having computer-executable instructions embodied thereon that, when executed, perform a method of integrating nodes of disease treatment decision criteria to be satisfied into an electronic medical record (EMR) of a patient, the method comprising the steps of:

receiving a disease treatment decision tree from a third-party resource for a particular type of disease diagnoses;

creating nodes of disease treatment decision criteria based on the disease treatment decision tree for the patient to be satisfied to determine a medical course of action;

integrating the nodes of the decision criteria into the EMR of the patient;

providing pricing information for at least one node of the series of branching nodes;

causing for display on a graphical user interface of a computing device a plurality of clickable icons, each clickable icon of the plurality of clickable icons representing a communication of a set of communications associated with information related to the medical course of action, the set of communications comprising one or more communications;

automatically determining there is updated information related to the medical course of action;

automatically updating the set of communications so that the updated information is included in the set of communications;

processing at least a portion of the series of branching nodes of the disease treatment decision tree;

ordering a medical procedure based on the medical course of action for the patient; and documenting that the medical procedure was ordered in the disease treatment decision tree in the EMR of the patient.

9. The method of claim 8, further comprising: causing for display on the graphical user interface of the computing device at least a portion of the medical treatment decision tree, wherein the pricing information associated with the at least one node of the series of branching nodes is displayed adjacent to the at least one node.

10. The method of claim 8, wherein one or more nodes comprise areas to make notes regarding the suggested medical course of action for the patient.

11. The method of claim 8, wherein one or more nodes comprise warnings, precautions, toxicities, and side effects of a medication.

12. The method of claim 8, wherein one or more orders are placed at one or more nodes in order to satisfy the suggested medical course of action for the patient.

13. The method of claim 8, wherein there are one or more nodes that are satisfied by placing one or more orders to satisfy the suggested medical course of action for the patient prior to reaching a final node.

14. The method of claim 8, wherein lab results and diagnostics of the patient are included at one or more nodes.

15. The method of claim 14, wherein pathology results, vitals and measurements of the patient are included at the one or more nodes.

16. The method of claim 1, further comprising: causing for display on the graphical user interface of the computing device at least a portion of the medical treatment decision tree, wherein the pricing information associated with the at least one node of the series of branching nodes is displayed adjacent to the at least one node.

17. The method of claim 1, further comprising: causing for display on the graphical user interface of the computing device at least a portion of the medical treatment decision tree, wherein the results of the medical procedure are displayed with the portion of the medical treatment decision tree displayed on the graphical user interface.

* * * * *

UNITED STATES PATENT AND TRADEMARK OFFICE
CERTIFICATE OF CORRECTION

PATENT NO. : 10,665,343 B1
APPLICATION NO. : 14/585498
DATED : May 26, 2020
INVENTOR(S) : Mark A. Davenport et al.

Page 1 of 1

It is certified that error appears in the above-identified patent and that said Letters Patent is hereby corrected as shown below:

In the Drawings

Sheet 2 of 15, FIG. 2A.: Please remove "Hormonal Threapy" and replace with --Hormonal Therapy--.

In the Claims

Column 14, Line 24: Please remove "The method of claim 8, further comprising" and replace with --The one or more non-transitory computer-storage media of claim 8, wherein the method further comprises--.

Column 14, Line 30: Please remove "The method" and replace with --The one or more non-transitory computer-storage media--.

Column 14, Line 33: Please remove "The method" and replace with --The one or more non-transitory computer-storage media--.

Column 14, Line 37: Please remove "The method" and replace with --The one or more non-transitory computer-storage media--.

Column 14, Line 40: Please remove "The method" and replace with --The one or more non-transitory computer-storage media--.

Column 14, Line 45: Please remove "The method" and replace with --The one or more non-transitory computer-storage media--.

Column 14, Line 47: Please remove "The method" and replace with --The one or more non-transitory computer-storage media--.

Signed and Sealed this
Third Day of November, 2020

Andrei Iancu
*Director of the United States Patent and Trademark Office*